United States Patent [19]

Whitney

[11] 4,372,964

[45] Feb. 8, 1983

[54] ANTIINFLAMMATORY 4,5-DIARYL-1H-IMIDAZOLE-2-METHANOLS

[75] Inventor: Joel G. Whitney, Kennett Square, Pa.

[73] Assignee: E. I. Du Pont de Nemours and Company, Wilmington, Del.

[21] Appl. No.: 294,747

[22] Filed: Aug. 20, 1981

Related U.S. Application Data

[63] Continuation-in-part of Ser. No. 199,731, Oct. 30, 1980, abandoned, which is a continuation-in-part of Ser. No. 181,991, Aug. 28, 1980, abandoned, which is a continuation-in-part of Ser. No. 109,923, Jan. 7, 1980, abandoned.

[51] Int. Cl.³ .................. A61K 31/415; C07D 233/64
[52] U.S. Cl. .................. 424/273 R; 424/263; 546/256; 546/278; 548/336; 548/342; 548/343
[58] Field of Search ............ 546/256, 278; 548/336, 548/342; 424/263, 273 R

[56] References Cited

U.S. PATENT DOCUMENTS

| | | | |
|---|---|---|---|
| 3,197,480 | 7/1965 | England | 260/326.5 |
| 3,258,466 | 6/1966 | Kawakami | 548/341 |
| 3,350,364 | 10/1967 | Reimschuessel | 528/313 |
| 3,519,638 | 7/1970 | Kawakami | 548/341 |
| 3,622,584 | 11/1971 | Doebel et al. | 424/263 X |
| 3,658,991 | 4/1972 | Doebel et al. | 424/273 R |
| 3,707,475 | 12/1972 | Lombardino | 260/309 |
| 4,190,666 | 2/1980 | Cherkofsky et al. | 424/274 |

FOREIGN PATENT DOCUMENTS

| | | | |
|---|---|---|---|
| 2164919 | 7/1973 | Fed. Rep. of Germany | 548/341 |
| 1381031 | 1/1975 | United Kingdom | 548/346 |

*Primary Examiner*—Richard A. Schwartz

[57] ABSTRACT

Antiinflammatory 4,5-diaryl-1H-imidazole-2-methanols, such as 4,5-bis(4-fluorophenyl)-$\alpha,\alpha$-di(trifluoromethyl)-1H-imidazole-2-methanol are useful in treatment of arthritis.

36 Claims, No Drawings

ANTIINFLAMMATORY 4,5-DIARYL-1H-IMIDAZOLE-2-METHANOLS

CROSS-REFERENCE TO RELATED APPLICATIONS

This application is a continuation-in-part of U.S. patent application Ser. No. 199,731, filed Oct. 30, 1980, now abandoned, which is a continuation-in-part of U.S. patent application Ser. No. 181,991, filed Aug. 28, 1980, now abandoned, which is a continuation-in-part of U.S. patent application Ser. No. 109,923, filed Jan. 7, 1980, now abandoned.

BACKGROUND OF THE INVENTION

This invention relates to antiinflammatory imidazoles.

U.S. Pat. No. 4,190,666 discloses antiinflammatory 4,5-diaryl substituted imidazoles of the formula

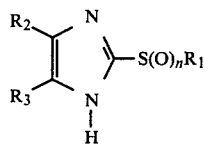

where $R_1$, $R_2$, and $R_3$ represent various defined groups, and n is an inteter of 0–2.

German DS 2164-919 discloses imidazole(2)carbinols of the formula

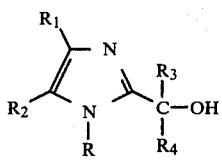

where

R, $R_1$, $R_2$, $R_3$ and $R_4$ represent various defined groups. The compounds are stated to have hypocholesteraemic activity and also are able to lower the triglyceride level in blood serum.

D. C. England, U.S. Pat. No. 3,197,480 includes disclosure of the compound:

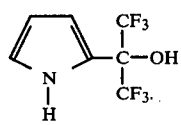

Pharmaceutical use for the compounds of this patent is not disclosed.

There is a continuing need for safe and effective antiinflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment. The usefulness of most commercial antiinflammatories is limited because of toxicity and adverse side-effects. Many produce gastric irritation and other effects, such as changes in blood cells and central nervous system. Adreno-cortical steroids produce gastric irritation and suppresion of normal adrenal function.

In addition to antiinflammatory properties, compounds within the scope of this invention have demonstrated analgesic activity in a test procedure. This additional property is desirable in treatment of arthritis or related diseases; however, the compounds which exhibit this property can be employed solely to alleviate pain.

SUMMARY OF THE INVENTION

This invention relates to compounds of formula I, pharmaceutical compositions containing them, and methods of use of these compounds to treat arthritis,

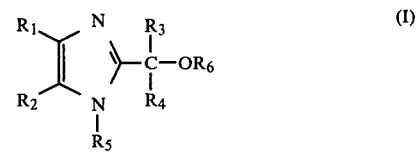

wherein $R_1$ and $R_2$ independently are 3-pyridyl, 2-thienyl or

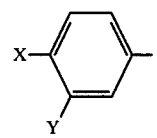

where

X is H, F, Cl, Br, $C_1$–$C_2$ alkyl, $C_1$–$C_2$ alkoxy, di($C_1$–$C_2$ alkyl)amino or $CH_3S(O)_n$;

n=0, 1 or 2;

Y is H, F or Cl with the proviso that when Y is F or Cl, then X must be F or Cl;

$R_3$ and $R_4$ independently are H, $C_1$–$C_3$ alkyl, cyclopropyl, $CF_3$, $CF_2H$, $CF_2Cl$, $CF_3CF_2$ or $CF_3CF_2CF_2$; with the proviso that no more than one of $R_3$ and $R_4$ can be H;

$R_5$=H or $C_1$–$C_3$ alkyl;

$R_6$=H; $C_1$–$C_3$ alkyl;

or —$COOR_7$;

where $R_7$ is $C_1$–$C_2$ alkyl;

with the proviso that $R_5$ and $R_6$ cannot both be $C_1$–$C_3$ alkyl; or a pharmaceutically suitable acid addition salt where $R_1$ or $R_2$ is 3-pyridyl or where X is dialkylamino, or a pharmaceutically suitable metal salt when at least one of $R_5$ and $R_6$ is H.

In addition to antiinflammatory properties, some of the compounds of formula I also possess analgesic properties.

Also, the present invention is directed to novel intermediates of Formula II useful in the preparation of antiinflammatory compounds of Formula I. Compounds of Formula II possess antiinflammatory activity themselves and some of the compounds of Formula II also possess analgesic properties,

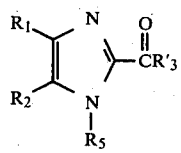 II where

R₁ and R₂ independently are 3-pyridyl, 2-thienyl or

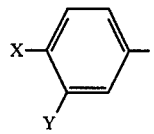

where

X is H, F, Cl, Br, $C_1$-$C_2$ alkyl, $C_1$-$C_2$ alkoxy, di($C_1$-$C_2$ alkyl)amino or $CH_3S(O)_n$; n=0, 1 or 2;

Y is H, F or Cl with the proviso that when Y is F or Cl, then X must be F or Cl;

R'₃ is $C_1$-$C_3$ alkyl, cyclopropyl, $CF_3$, $CF_2H$, $CF_2Cl$, $CF_3CF_2$ or $CF_3CF_2CF_2$;

R₅ is H or $C_1$-$C_3$ alkyl.

PREFERRED COMPOUNDS

Preferred Formula I compounds for utility considerations or ease of synthesis are those compounds in which, independently, (a) R₁ and R₂ independently =

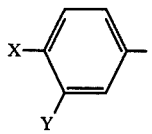

where

X=F or $CH_3O$ and Y is H; or (b) R₃ and R₄ independently are H, $CH_3$, $CH_3CH_2$, $CF_3$, $CF_2Cl$, $CF_2H$, or $CF_2CF_3$; or (c) R₅ is H; or (d) R₆ is H or $CH_3$.

More preferred for their high degree of biological activity are those compounds in which R₁ and R₂ independently =

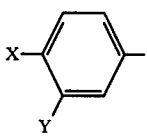

where

X is F or $CH_3O$; and
Y is H; and
R₃ and R₄ independently are H, $CH_3$, $CH_2CH_3$, $CF_3$, $CF_2Cl$, $CF_2H$ or $CF_2CF_3$; and
R₅=H; and
R₆=H or $CH_3$.

Preferred compounds are:

4,5-bis(4-fluorophenyl)-α,α-di(trifluoromethyl)-1H-imidazole-2-methanol;

4,5-bis(4-fluorophenyl)-α-methyl-α-trifluoromethyl-1H-imidazole-2-methanol;

4,5-bis(4-fluorophenyl)-α-difluoromethyl-α-trifluoromethyl-1H-imidazole-2-methanol;

4,5-bis(4-fluorophenyl)-α-methyl-α-pentafluoroethyl-1H-imidazole-2-methanol; and 4,5-bis(4-fluorophenyl)-α-ethyl-α-trifluoromethyl-1H-imidazole-2-methanol.

Preferred compounds of Formula I for their analgesic properties are those compounds in which R₁ and R₂ are both 4—$CH_3OC_6H_4$—; R₃ and R₄ independently are H, $CH_3$, $CH_2CH_3$, $CF_2H$, $CF_3$ or $CF_2CF_3$; R₅ is H; and R₆ is H or $CH_3$, Preferred compounds possessing analgesic properties are:

4,5-bis(4-methoxyphenyl)-α,α-di(trifluoromethyl)-1H-imidazole-2-methanol;

4,5-bis(4-methoxyphenyl)-α-difluoromethyl-α-trifluoromethyl-1H-imidazole-2-methanol;

4,5-bis(4-methoxyphenyl)-α-methyl-α-trifluoromethyl-1H-imidazole-2-methanol;

4,5-bis(4-methoxyphenyl)-α-trifluoromethyl-1H-imidazole-2-methanol;

4,5-bis(4-methoxyphenyl)-α-methyl-α-pentafluoroethyl-1H-imidazole-2-methanol; and 4,5-bis(4-methoxyphenyl)-α,α-dimethyl-1H-imidazole-2-methanol.

Preferred Formula II compounds for utility considerations or ease of synthesis are those in which, independently, (a) R₁ and R₂ independently =

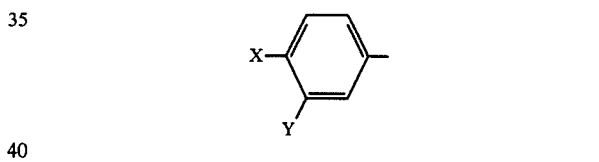

where X=F or $CH_3O$ and Y=H; or (b) R'₃ is $CF_3$ or $CF_2CF_3$; or (c) R₅ is H or $CH_3$.

Specifically preferred compounds of Formula II are:

1-[4,5-bis(4-methoxyphenyl)-1H-imidazol-2-yl]-2,2,2-trifluoro-1-ethanone;

1-[4,5-bis(4-methoxyphenyl)-1-methyl-1H-imidazol-2-yl]-2,2,2-trifluoro-1-ethanone;

1-[4,5-bis(4-fluorophenyl)-1H-imidazol-2-yl]-2,2,2-trifluoro-1-ethanone;

1-[4,5-bis(4-methoxyphenyl)-1H-imidazol-2-yl]-2,2,3,3,3-pentafluoro-1-propanone; and 1-[4,5-bis(4-fluorophenyl)-1H-imidazol-2-yl]-2,2,3,3,3-pentafluoro-1-propanone.

SYNTHESIS

Compounds of Formula I where R₅=H and R₆=H can be prepared by contacting an N-protected 4,5-disubstituted imidazole with a strong base, such as n-butyl lithium, in an inert solvent at low temperature, followed by a ketone or aldehyde and then removal of the protecting group. The nature of the N-protecting group is such that it is stable to strong bases, but easily removed by acidic reagents. Examples of useful protecting groups are 2-tetrahydropyranyl, benzyloxymethyl, methoxymethyl, methylthiomethyl, β-methoxyethoxymethyl, 2-tetrahydrofuranyl and α-ethoxyethyl.

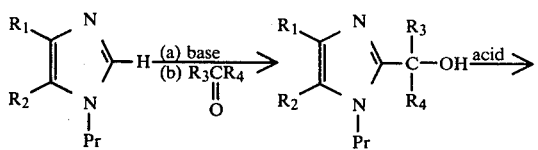

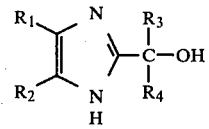

(Pr = protecting group)

Compounds of Formula I where $R_5$ is not H can similarly be prepared by using the appropriate $R_5$ as a protecting group.

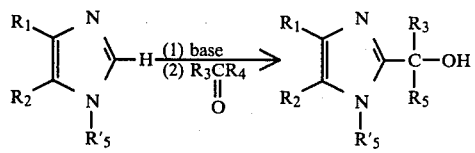

($R'_5$ = $C_1$-$C_3$ alkyl)

The syntheses of 4,5-disubstituted imidazoles substituted in the 1-position with an $R'_5$ group or with a protecting group are described in U.S. Pat. Nos. 4,159,338; 4,182,769; 4,190,166; and 4,199,592.

Alternatively, compounds of formula I with at least one of $R_3$ or $R_4$=H, $C_1$-$C_3$ alkyl or cyclopropyl can be prepared from 1-(4,5-disubstituted-1H-imidazol-2-yl)-1-alkanones by treatment with reducing agents (sodium borohydride or the like) or organometallic reagents (Grignard reagents or the like) and removal of the protecting group if present.

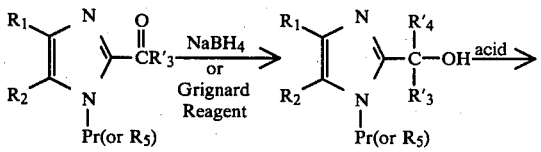

($R'_4$ = H, $C_1$-$C_3$ alkyl or cyclopropyl)

The 1-(4,5-disubstituted-1H-imidazol-2-yl)-1-alkanones can be prepared from the corresponding N-substituted 4,5-disubstituted 1H-imidazoles by treatment with a strong base, such as n-butyl lithium, in an inert solvent at low temperature, followed by an acid anhydride or an N,N-disubstituted acid amide, followed by removal of the N-protecting group if present.

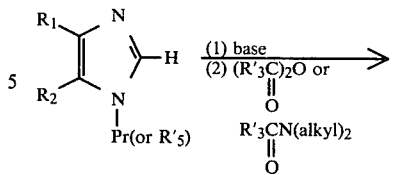

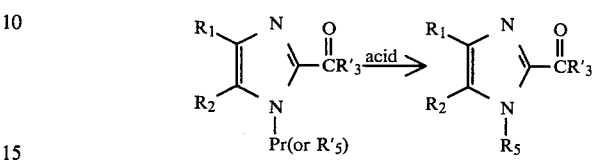

Compounds of Formula I with $R_6$=$C_1$-$C_3$ alkyl can be prepared from the N-protected compounds with $R_6$=H by direct alkylation followed by removal of the protecting group. These alkylations can be conducted in the presence of a base, such as potassium carbonate, pyridine, triethylamine, potassium t-butoxide, sodium hydride or the like, in an inert solvent such as dimethylformamide or the like. (L signifies an appropriate leaving group, such as halide or sulfonate).

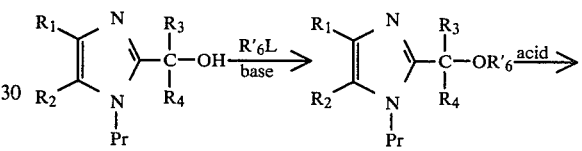

($R'_6$ = $C_1$-$C_3$ alkyl)

Compounds of Formula I with $R_6$=

or —COOR$_7$ can be prepared from the compounds with $R_6$=H by treatment with an acid chloride or acid anhydride in the absence or presence of a base, such as potassium t-butoxide.

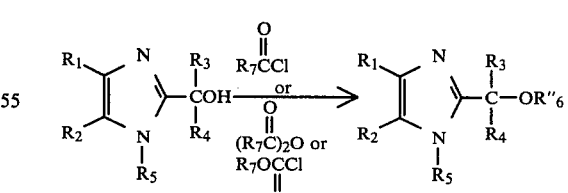

($R''_6$ = —$\overset{O}{\overset{\|}{C}}R_7$ or —$\overset{O}{\overset{\|}{C}}OR_7$)

Pharmaceutically suitable salts of the compounds of Formula I can be of two types. First, when one or both of $R_1$ and $R_2$ is a dialkylaminophenyl or a 3-pyridyl group, acid addition salts can be prepared by treatment of the free base I with the appropriate acid. Second, pharmaceutically suitable metal salts (forming the salt of the acidic OH or NH) can be prepared by treatment of compounds of Formula I (when at least one of $R_5$ and $R_6$ is H) with strong bases such as hydroxides, hydrides, alkoxides or the like.

In the following examples, all parts are by weight and temperatures are in degrees Centigrade unless otherwise specified. The unnumbered compounds in Tables 1 and 2 represent unprepared embodiments of this invention. Preparation of these compounds by the process described herein will be substantially routine.

EXAMPLE 1

4,5-Bis(4-fluorophenyl)-α,α-di(trifluoromethyl)-1H-imidazole-2-methanol

A mixture of 56.0 g (0.22 mole) of 4,5-bis-(4-fluorophenyl)imidazole, 26.0 g (0.2 mole) of dichloroacetic acid and 30.0 g (0.42 mole) of ethyl vinyl ether in 200 ml of toluene was heated at reflux overnight. The reaction mixture was allowed to cool to room temperature and was then stirred with 200 ml of 2 N aqueous sodium hydroxide overnight. The organic layer was separated, washed with water and then dried over anhydrous potassium carbonate. Removal of the solvent under vacuum gave 66.1 g of an oil. Chromatography on basic alumina (Woelm activity grade I) and crystallization with cyclohexane gave 36.5 g of 4,5-bis(4-fluorophenyl)-1-(α-ethoxyethyl)imidazole, m.p. 105°–107°. The infrared and NMR spectra were consistent with the assigned structure.

Anal. Calcd. for $C_{19}H_{18}F_2N_2O$: C, 69.51; H, 5.49; N, 8.54; Found: C, 69.5; H, 5.27; N, 8.32.

To a stirred solution of 10.0 g (30.5 mmoles) of 4,5-bis(4-fluorophenyl)-1-(α-ethoxyethyl)imidazole and 3.9 g (33.6 mmoles) of tetramethylethylenediamine in 150 ml of THF under an atmosphere of nitrogen and cooled at −78° was added dropwise 30 ml of 1.6 M butyl lithium solution. After stirring for 10 minutes, 5 ml (7.5 g, 45.2 mmoles) of hexafluoroacetone was added dropwise. The reaction mixture was stirred for 1 hour, with continued cooling and then 100 ml of a saturated aqueous sodium bicarbonate solution was added dropwise. The mixture was allowed to warm to room temperature and the organic layer was separated. The solvent was evaporated and the residue distributed between ether and a saturated aqueous sodium bicarbonate solution. The ether layer was evaporated and the residue stirred with 200 ml of ethanol and 100 ml of 2 N aqueous hydrochloric acid overnight. The product was extracted into ether, which, after washing with water, was dried and concentrated in vacuo to afford 11.3 g of a semisolid. Crystallization from hot 1-chlorobutane gave 6.3 g of 4,5-bis(4-fluorophenyl)-α,α-di(trifluoromethyl)-1H-imidazole-2-methanol, m.p. 153°–155°. The infrared and NMR spectra were consistent with the assigned structure.

Anal. Calcd. for $C_{18}H_{10}F_8N_2O$: C, 51.2; H, 2.4; N, 6.64; Found: C, 51.6; H, 2.56; N, 6.49.

EXAMPLE 2

4,5-Bis(4-methoxyphenyl)-α,α-di(trifluoromethyl)-1H-imidazole-2-methanol

By the procedure described in Example 1, 4,5-bis(4-methoxyphenyl)imidazole was converted to 4,5-bis(4-methoxyphenyl)-1-(α-ethoxyethyl)imidazole. The NMR was consistent with the structure.

Reaction with hexafluoroacetone according to the procedure of Example 1, gave 4,5-bis(4-methoxyphenyl)-α,α-di(trifluoromethyl)-1H-imidazole-2-methanol, m.p. 144°–146°. The infrared and NMR spectra were consistent with the assigned structure.

Anal. Calcd. for $C_{20}H_{16}F_6N_2O_3$: C, 53.8; H, 3.6; N, 6.3; Found: C, 54.2; H, 3.67; N, 5.72.

EXAMPLE 3

4,5-Bis(4-fluorophenyl)-α-methyl-α-trifluoromethyl-1H-imidazole-2-methanol

By the procedure described in the second paragraph of Example 1, 4,5-bis(4-fluorophenyl)-1-(α-ethoxyethyl)imidazole was reacted with 1,1,1-trifluoroacetone to give 4,5-bis(4-fluorophenyl)-α-methyl-α-trifluoromethyl-1H-imidazole-2-methanol, m.p. 191°–192°. The infrared and NMR spectra were consistent with the assigned structure.

Anal. Calcd. for $C_{18}H_{13}F_5N_2O$: C, 58.7; H, 3.53; N, 7.6. Found: C, 58.7; H, 3.60; N, 7.62.

EXAMPLE 4

4,5-Bis(4-methoxyphenyl)-1-methyl-α,α-(trifluoromethyl)-1H-imidazole-2-methanol

A solution of 10.0 g. 4,5-bis(4-methoxyphenyl)imidazole in 100 ml of dimethylformamide was treated with 2.4 g of a 50% sodium hydride dispersion and then 8.0 g of methyl iodide was added dropwise. Stirring at room temperature was continued overnight and the reaction mixture was poured onto ice water. The product was collected by filtration and recrystallization from hot 1-chlorobutane gave 7.0 g of 4,5-bis(4-methoxyphenyl)-1-methyl-1H-imidazole, m.p. 121.5°–122°.

Anal. Calcd. for $C_{18}H_{18}N_2O_2$: C, 73.47; H, 6.12; N, 9.52. Found: C. 73.5; H, 6.23; N, 9.49.

By the procedure described in the second paragraph of Example 1, 4,5-bis(4-methoxyphenyl)-1-methyl-1H-imidazole was converted to 4,5-bis(4-methoxyphenyl)-1-methyl-α,α-di(trifluoromethyl)-1H-imidazole-2-methanol, m.p. 147°–147.5°. The NMR spectrum was consistent.

Anal. Calcd. for $C_{21}H_{18}F_6N_2O_3$: C, 54.78; H, 3.91; N, 6.1. Found: C, 55.0; H, 3.89; N, 5.86.

EXAMPLE 5

4,5-Bis(4-methoxyphenyl)-1-methyl-α,α-di(trifluoromethyl)-1H-imidazole-2-methanol, Acetate A solution of 2.3 g (5 mmoles) of 4,5-bis(4-methoxyphenyl)-1-methyl-α,α-di(trifluoromethyl)-1H-imidazole-2-methanol in 20 ml of acetic anhydride was heated under reflux for 4 hours. The acetic anhydride was then removed under vacuo on a rotary evaporator. Oxylene (50 ml) was then added, and evaporated under vacuo. This was repeated one more time. The residue was then recrystallized from methyl cyclohexane to give 2.0 g of the title compound, m.p. 121°–123°. The infrared and NMR spectra were consistent with the assigned structure.

Anal. Calcd. for $C_{23}H_{20}F_6N_2O_4$: C, 54.98; H, 4.01; N, 5.57. Found: C, 55.0; H, 4.01; N, 5.6.

EXAMPLE 6

4,5-Bis(4-methoxyphenyl)-1-methyl-α,α-di(trifluoromethyl)-1H-imidazole-2-methanol, Ethylcarbonate To a stirred solution of 2.3 g (5 mmoles) of 4,5-bis(4-methoxyphenyl)-1-methyl-α,α-di(trifluoromethyl)-1H-imidazole-2-methanol in 40 ml of glyme chilled to 10°, was added 0.85 g (7.5 mmoles) of potassium tert.butoxide. After 15 minutes, a solution of 0.85 g (~7.5 mmoles; 0.75 ml) of ethyl chloroformate in 10 ml of glyme was added in the cold dropwise. After stirring at 10° for one hour, the reaction mixture was stirred overnight. The solvent was removed by evaporation under vacuo, then the residue was dissolved in 200 ml of methylene chloride, washed with water, dried over anhydrous magnesium sulfate, and the filtered extract evaporated to dryness to yield a solid residue. Recrystallization from methyl cyclohexane, yielded 2.0 g of the title compound, m.p. 148°-150°. The infrared and NMR spectra were consistent with the assigned structure.

Anal. Calcd. for $C_{24}H_{22}F_6N_2O_5$: C, 54.14; H, 4.16; N, 5.26. Found: C, 54.8; 54.9: H, 4.3, 4.3; N, 5.1, 5.1.

EXAMPLE 7

4,5-Bis(4-methoxyphenyl)-2-[1-methoxy-2,2,2-trifluoro-1-(trifluoromethyl)ethyl]-1H-imidazole To a stirred solution of 20.0 g (60.25 mmoles) 4,5-bis(4-methoxyphenol)-1-(α-ethoxyethyl)-1H-imidazole, and 7.8 g (67.2 mmoles) of tetramethylethylenediamine in 300 ml of THF under an atmosphere of nitrogen and cooled to −78° was added dropwise 60 ml of 1.6 M n-butyl lithium solution. After stirring for 15 minutes, 10 ml (15.0 g, 90.4 mmoles) of hexafluoroacetone was added dropwise. The reaction mixture was stirred for 1 hour, with continued cooling, and then 200 ml of a saturated aqueous sodium bicarbonate solution was added dropwise. The mixture was allowed to warm to room temperature and the organic layer was separated. The solvent was evaporated, and the residue dissolved in 500 ml of ether. The organic layer was washed with 300 ml of saturated sodium bicarbonate solution, followed by water, dried over anhydrous magnesium sulfate, filtered and evaporated. The residue was then redissolved in 200 ml of anhydrous DMF, and allowed to react with methyl iodide (10 g) in the presence of 15 g anhydrous potassium carbonate by stirring overnight. The DMF was removed by evaporation under vacuo, and the residue was treated with 300 ml of water. The organic components were extracted with 500 ml of ether. The organic layer was washed with water and dried over anhydrous magnesium sulfate. The concentrated ether extract was then chromatographed on a column of silica gel (300 g) and eluted with a solvent mixture consisting of 90 parts toluene and 10 parts ethyl acetate. The desired fractions were pooled and evaporated to yield 10 g of residue. The ethoxy ethyl protecting group was cleaved by acidic hydrolysis, carried out by stirring the residue with a mixture consisting of 200 ml ethanol and 100 ml of 1 N HCl overnight. the reaction mixture was neutralized with saturated aqueous sodium bicarbonate, and the product was extracted with 500 ml methylene chloride, washed with water, and dried over anhydrous magnesium sulfate. The inorganic salts were removed by filtration, and the filtrate was evaporated. The residue was then recrystallized from methyl cyclohexane to yield 6 g of the title compound, m.p. 129°-131°. The infrared and NMR spectra were consistent with the assigned structure. Mass spectrum: Calc.: 460: Found: 460.

Anal. Calcd for $C_{21}H_{18}N_2O_3F_6$: C, 54.8; H, 3.94; N, 6.1. Found: C, 55.6; 55.8; H, 4.0, 4.0; N, 6.1, 6.5

EXAMPLE 8

1-[4,5-Bis(4-fluorophenyl)-1H-imidazol-2-yl]-2,2,2-trifluoro-1-ethanone

To a cooled (−78°) suspension of 5.0 g (14.7 mmoles) of 4,5-bis(4-fluorophenyl)-1-(2-tetrahydropyranyl)-1H-imidazole in 75 ml of ether containing 1.9 g (16.4 mmoles) of tetramethylethylenediamine was added dropwise 18.0 ml (28.8 mmoles) of a 1.6 M solution of n-butyl lithium. After stirring at −78° for 10 minutes, a solution of 6.1 g (29 mmoles) of trifluoroacetic anhydride in 25 ml of ether was added dropwise. The reaction mixture was allowed to warm to room temperature and then washed with 10% aqueous sodium bicarbonate solution. The ether layer was dried and evaporated. The oily residue was purified by chromatography on silica gel using toluene as the eluent to give 1.65 g of 1-[4,5-bis(4-fluorophenyl)-1-(2-tetrahydropyranyl)-1H-imidazol-2-yl]-2,2,2-trifluoro-1-ethanone as a semicrystalline colorless oil.

The intermediate product was stirred with a mixture of 20 ml of ethanol and 10 ml of 1 N hydrochloric acid at room temperature overnight. The reaction mixture was poured onto water and the product extracted into ether. The combined organic extracts were washed with water, dried and concentrated under vacuum. The residual oil was purified by chromatography on silica gel using chloroform or toluene as the eluent. The product fraction was crystallized from toluene/hexane (1:4) to give 700 mg of the title compound as colorless crystals, m.p. 214°-215.5°. The proton and fluorine NMR spectra were consistent with the assigned structure.

Anal.. Calcd. for $C_{17}H_9F_5N_2O$: C, 57.95; H, 2.56; N, 7.95. Found: C, 58.31; 58.26; H, 2.77; 2.77; N, 7.84; 7.84.

EXAMPLE 9

1-[4,5-Bis(4-methoxyphenyl)-1H-imidazol-2-yl]2,2,2-trifluoro-1-ethanone

To a stirred solution of 14.12 g (40 mmoles) 4,5-bis(4-methoxyphenyl)-1-(α-ethoxyethyl)imidazole and 4.64 g tetramethylethylenediamine in 100 ml of dry THF under an atmosphere of nitrogen and cooled at −78° was added dropwise 30 ml of 1.6 M n-butyl lithium solution. After stirring for 15 minutes, a solution of 5.7 g (40.1 mmoles) N,N-dimethyltrifluoroacetamide in 30 ml of dry THF was added dropwise. After the addition was complete, the reaction mixture was stirred for 1 hour, with continued cooling, and then 150 ml of a saturated aqueous sodium bicarbonate solution was added dropwise. The mixture was allowed to warm to room temperature. The THF was removed by evaporation under vacuo on a rotary evaporator. The organic components were then extracted with 400 ml of methylene chloride, washed with 100 ml of a saturated solution of sodium bicarbonate, followed by water, and the organic extract was dried over magnesium sulfate. The inorganic salts were removed by filtration, and the solvent was removed by evaporation. The residue was chromatographed on a column of 250 g silica gel, eluting with a solvent mixture consisting of 90 parts toluene and 10 parts ethyl acetate. The chromatographed product thus obtained was crystallized from methyl cyclohexane to give 9 g of 1-[4,5-bis(4-methoxyphenyl)-1-(α-ethoxyethyl)-1H-imidazol-2-yl]2,2,2-trifluoro-1-ethanone, m.p. 124°-126°. Infrared and NMR spectra were consistent with the assigned structure.

A solution of 6 g of the above intermediate in 150 ml ethanol was mixed with 100 ml of 1 N HCl, and the mixture stirred at room temperature overnight. Most of the ethanol was removed by evaporation under vacuo. The mineral acid present was then neutralized by the addition of aqueous sodium bicarbonate to pH ~8. A flocculent yellow material which formed was collected by filtration, washed and dried. Recrystallization from methylcyclohexane yielded 5.0 g of the title compound, m.p. 191°–192°. The infrared and NMR spectra were consistent with the assigned structure.

Anal. Calcd for $C_{19}H_{15}F_3N_2O_3$: C, 60.64; H, 4.0; N, 7.4; Found: C, 60.7; H, 4.1; N, 7.3.

EXAMPLE 10

4,5-Bis(4-methoxyphenyl)-α-(trifluoromethyl)-1H-imidazole-2-methanol

To a stirred solution of 3.8 g (10 mmoles) of the compound of Example 9 in 50 ml ethanol chilled to 0°–5°, was added 1.0 g (25 mmoles) sodium borohydride all at once. After 0.5 hour at that temperature, the cooling was discontinued, and the reaction was allowed to proceed at room temperature for 1 hour. The reaction mixture was then chilled to 0°–10° C., and 40 ml of 2 N HCl was cautiously added, followed by another 40 ml of water. Most of the ethanol was removed under vacuo. The crystalline product was collected by filtration, washed with water, and air dried. Recrystallization from acetonitrile yielded 3.9 of the title compound, m.p. 242°–245°. The infrared and NMR spectra were consistent with the assigned structure.

Anal. Calcd. for $C_{19}H_{17}F_3N_2O_3 \cdot H_2O$: C, 55.07, H. 5.1, N, 6.7. Found: C, 55.1, 55.0; H, 4.3, 4.3; N, 6.7, 6.7.

EXAMPLE 11

4,5-Bis(4-Fluorophenyl)-α-methyl-α-/pentafluoroethyl-1H-imidazole-2-methanol To a stirred solution of 1-[4,5-bis(4-fluorophenyl)-1H-imidazol-2-yl]-2,2,3,3,3-pentafluoro-1-propanone (1.5 gm ~4 millimoles) [prepared by the general procedure of Examples 8 and 9] in anhydrous tetrahydrofuran, a solution of methyl magnesium chloride (10 ml 1.6 molar) was added, and the reaction mixture stirred overnight. Excess unreacted Grignard reagent was decomposed by the addition of saturated ammonium chloride (15 ml). The gelatinous magnesium salts were filtered off, and the filter cake hot extracted with 50 ml of tetrahydrofuran, and then filtered to remove inorganic salts. The solvent was evaporated, and the residue dissolved in chloroform, washed with water, and the solvent evaporated. The material obtained was recrystallized from methyl cyclohexane, to give product, 162° to 164°.

The mass spectrum, and the N.M.R. were consistent with the above assigned structure.

Following the procedures given in Examples 1–7 and 10–11, the following compounds of Formula I can be prepared:

TABLE 1

$$\begin{array}{c} R_1 \\ R_2 \end{array} \begin{array}{c} N \\ \diagdown \\ N \\ | \\ R_5 \end{array} \begin{array}{c} R_3 \\ | \\ C-OR_6 \\ | \\ R_4 \end{array} \qquad I$$

| EXAMPLE | $R_1$ | $R_2$ | $R_3$ | $R_4$ | $R_5$ | $R_6$ | m.p. °C. |
|---|---|---|---|---|---|---|---|
| 12 | 4-$CH_3OC_6H_4$ | 4-$CH_3OC_6H_4$ | $CF_3$ | $CF_2Cl$ | H | H | 134–136° |
| 13 | 4-$CH_3OC_6H_4$ | 4-$CH_3OC_6H_4$ | $CF_2Cl$ | $CF_2Cl$ | H | H | 135–137° |
| 14 | 4-$FC_6H_4$ | 2-thienyl | $CF_3$ | $CF_3$ | H | H | 114–115° |
| 15 | 4-$CH_3OC_6H_4$ | 4-$CH_3OC_6H_4$ | $CF_3$ | $CF_2H$ | H | H | 138–140° |
| 16 | 4-$FC_6H_4$ | 4-$FC_6H_4$ | $CF_3$ | $CF_2H$ | H | H | 166–167° |
| 17 | $C_6H_5$ | 3,4-$Cl_2C_6H_3$ | $CF_3$ | $CF_3$ | H | H | oil |
| 18 | 4-$CH_3OC_6H_4$ | 4-$CH_3OC_6H_4$ | $CF_3$ | $CH_3$ | H | H | 192–193° |
| 19 | 4-$CH_3OC_6H_4$ | 4-$CH_3OC_6H_4$ | $CF_3$ | H | $CH_3$ | H | 181–183° |
| 20 | $C_6H_5$ | $C_6H_5$ | $CF_3$ | $CF_3$ | H | H | 115–116° |
| 21 | 4-$FC_6H_4$ | 4-$CH_3SC_6H_4$ | $CF_3$ | $CF_3$ | H | H | 179–181° |
| 22 | 4-$ClC_6H_4$ | 4-$ClC_6H_4$ | $CF_3$ | $CF_3$ | H | H | 151–152° |
| 23 | 4-$FC_6H_4$ | 4-$FC_6H_4$ | $CF_3CF_2$ | H | H | H | 227–228° |
| 24 | 4-$FC_6H_4$ | 4-$CH_3SC_6H_4$ | $CF_3$ | $CH_3$ | H | H | 182–183° |
| 25 | 4-$FC_6H_4$ | 4-$FC_6H_4$ | $CF_3$ | $CF_3$ | H | $C(O)CH_3$ | 133–135° |
| 26 | 4-$FC_6H_4$ | 4-$FC_6H_4$ | $CH_3$ | $CH_3$ | $CH_3$ | H | 140–141° |
| 27 | 4-$FC_6H_4$ | 4-$FC_6H_4$ | $CF_3$ | H | H | H | 249–252° |
| 28 | 4-$FC_6H_4$ | 4-$FC_6H_4$ | $CH_3$ | $CH_3$ | H | H | 228–232° |
| 29 | 4-$CH_3OC_6H_4$ | 4-$CH_3OC_6H_4$ | $CF_3CF_2$ | $CH_3$ | H | H | 175–176° |
| 30 | 4-$CH_3OC_6H_4$ | 4-$CH_3OC_6H_4$ | $CH_3$ | $CH_3$ | H | H | 173–174° |
| 31 | 4-$FC_6H_4$ | 4-$FC_6H_4$ | $CF_3$ | $CH_3CH_2$ | H | H | 160–161° |
| 32 | 4-$FC_6H_4$ | 4-$FC_6H_4$ | $CF_3$ | $CH_3CH_2CH_2$ | H | H | 141–142° |
| 33 | 4-$CH_3OC_6H_4$ | 4-$CH_3OC_6H_4$ | $CH_3$ | 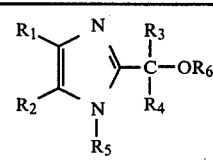 | H | H | 123–125° |
| 34 | 4-$CH_3OC_6H_4$ | 4-$CH_3OC_6H_4$ | $CH_3$ | $CH_3CH_2$ | H | H | 108–109° |
| 35 | 4-$CH_3OC_6H_4$ | 4-$CH_3OC_6H_4$ | $CH_3$ | H | H | H | 178° |
|  | 4-$FC_6H_4$ | 4-$BrC_6H_4$ | $CF_3$ | $CF_2Cl$ | H | H |  |
|  | 4-$FC_6H_4$ | 3-pyridyl | $CF_3$ | $CF_3$ | H | H |  |
|  | 4-$CH_3C_6H_4$ | 4-$CH_3C_6H_4$ | $CF_3$ | $CF_3$ | H | H |  |
|  | 4-$FC_6H_4$ | 4-$(CH_3)_2NC_6H_4$ | $CF_3$ | $CF_3$ | H | H |  |
|  | 4-$FC_6H_4$ | 4-$CH_3SO_2C_6H_4$ | $CF_3$ | $CF_3$ | H | H |  |
|  | 4-$C_2H_5C_6H_4$ | 4-$C_2H_5C_6H_4$ | $CF_3$ | $CF_2H$ | H | H |  |
|  | 4-$C_2H_5OC_6H_4$ | 4-$C_2H_5OC_6H_4$ | $CF_3$ | $CF_2Cl$ | H | H |  |
|  | 3-F, 4-$ClC_6H_3$ | $C_6H_5$ | $CF_3$ | $CF_2H$ | H | H |  |
|  | 4-$CH_3OC_6H_4$ | 4-$FC_6H_4$ | $CF_3$ | H | H | H |  |

TABLE 1-continued

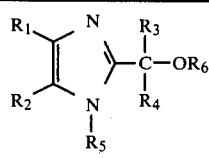

| EXAMPLE | R₁ | R₂ | R₃ | R₄ | R₅ | R₆ | m.p. °C. |
|---|---|---|---|---|---|---|---|
| | 4-FC₆H₄ | 4-FC₆H₄ | CF₂H | nC₃H₇ | H | H | |
| | 4-CH₃OC₆H₄ | 4-CH₃OC₆H₄ | CF₃ | CF₂CF₃ | H | H | |
| | 4-FC₆H₄ | 4-FC₆H₄ | CF₃CF₃CF₂ | H | H | H | |
| | 4-CH₃OC₆H₄ | 4-CH₃OC₆H₄ | CF₃ | CF₃ | C₂H₅ | H | |
| | 4-CH₃OC₆H₄ | 4-CH₃OC₆H₄ | CF₃ | CF₃ | nC₃H₇ | H | |
| | 4-CH₃OC₆H₄ | 4-CH₃OC₆H₄ | CF₃ | CF₃ | C₂H₅ | C(O)C₂H₅ | |
| | 4-CH₃OC₆H₄ | 4-CH₃OC₆H₄ | CF₃ | CF₃ | CH₃ | COOCH₃ | |
| | 4-FC₆H₄ | 4-FC₆H₄ | CF₃ | CF₃ | H | CH₃ | |
| | 4-FC₆H₄ | 4-FC₆H₄ | CF₃ | CF₃ | H | nC₃H₇ | |

Following the procedures given in Examples 8 and 9, the following compounds of Formula II can be prepared.

TABLE 2

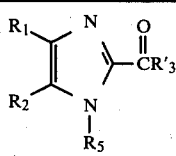

| EXAMPLE | R₁ | R₂ | R'₃ | R₅ | m.p. °C. |
|---|---|---|---|---|---|
| 36 | 4-CH₃OC₆H₄ | 4-CH₃OC₆H₄ | CF₃ | CH₃ | 144–146° |
| 37 | 4-FC₆H₄ | 4-CH₃SC₆H₄ | CF₃ | H | 179–181° |
| 38 | 4-CH₃OC₆H₄ | 4-CH₃OC₆H₄ | CF₃CF₂ | H | 184–186° |
| 39 | 4-FC₆H₄ | 4-FC₆H₄ | CF₃CF₂ | H | 197–200° |
| 40 | 4-CH₃OC₆H₄ | 4-CH₃OC₆H₄ | CH₃ | H | 191° |
| 41 | 4-FC₆H₄ | 4-FC₆H₄ | CH₃ | H | 210–211° |
| | 4-CH₃OC₆H₄ | 4-CH₃OC₆H₄ | CH₃CH₂CH₂ | H | |
| | 4-FC₆H₄ | 4-BrC₆H₄ | CF₃ | H | |
| | 4-C₂H₅C₆H₄ | 4-C₂H₅C₆H₄ | CF₃ | H | |
| | 4-C₂H₅OC₆H₄ | 4-C₂H₅OC₆H₄ | CF₃ | H | |
| | 4-ClC₆H₄ | 4-ClC₆H₄ | CF₃ | H | |
| | 3,4-Cl₂C₆H₃ | C₆H₅ | CF₃ | H | |
| | 4-FC₆H₄ | 4-(CH₃)₂NC₆H₄ | CF₃ | H | |
| | 4-FC₆H₄ | 4-CH₃SO₂C₆H₄ | CF₃ | H | |
| | 4-CH₃OC₆H₄ | 4-CH₃OC₆H₄ | CF₂H | H | |
| | 4-CH₃OC₆H₄ | 4-CH₃OC₆H₄ | CF₂Cl | H | |
| | 4-CH₃OC₆H₄ | 4-CH₃OC₆H₄ | CF₃CF₂CF₂ | H | |
| | 4-FC₆H₄ | 4-FC₆H₄ | CF₃ | nC₃H₇ | |

DOSAGE FORMS

The antiarthritic and analgesic agents of this invention can be administered to treat arthritis or relieve pain by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually, a daily dosage of active ingredient can be about 0.05 to 40 milligrams per kilogram of body weight. Ordinarily 0.1 to 20, and preferably 0.2 to 10 milligrams per kilogram per day given in divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions, the active ingredient will ordinarily be present in an amount of about 0.5 to 95% by weight based on the total weight of the composition.

The active ingredient can be administered orally in solid dosage forms such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propylparaben and chlorobutanol.

Suitable pharmaceutical carriers are described in *Remington's Pharmaceutical Sciences*, E. W. Martin, a standard reference text in this field.

Useful pharmaceutical dosage forms for administration of the compounds of this invention can be illustrated as follows:

Capsules

A large number of unit capsules are prepared by filling standard 2-piece hard gelatin capsules each with 50 milligrams of powdered active ingredient, 175 milligrams of lactose, 24 milligrams of talc, and 6 milligrams magnesium stearate.

A mixture of the active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increse palatability or delay absorption.

Injectable

A parenteral composition suitable for administration by injection is prepared by stirring 1.5% by weight of active ingredient in water with 0.75% sodium carboxymethylcellulose, 0.04% polysorbate 80, 0.9% benzyl alcohol, and 1.8% sodium chloride. The preparation is made sterile by autoclaving or other suitable techniques.

Suspension

An aqueous suspension is prepared for oral administration so that each 5 milliliters contain 10 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Use

To detect and compare the anti-inflammatory activities of compounds in this series and standard drugs, a test was used based on a standard model of arthritis for which there is good correlation with human efficacy. The model is adjuvant-induced arthritis in rats. *Federation Proceedings*, Vol. 32, No. 2, 1973, "Models Used for the Study and Therapy of Rheumatoid Arthritis'—Symposium of the American Society for Pharmacology and Experimental Therapeutics—states "The rat polyarthritis produced by intradermal injection of a suspension of *Mycobacterium tuberculosis* in mineral oil (adjuvant) has been used extensively for the screening of drugs of potential use in rheumatoid arthritis".

Compounds of this invention have shown activity in adjuvant-induced arthritis in rats which is widely recognized as a good model of human rheumatoid arthritis.

METHODS

Established Adjuvant-Induced Arthritis in Rats

Lewis (Wistar) male rats (Charles River Breeding Laboratories, Wilmington, Mass.) weighing 175–220 grams were injected subcutaneously with 0.1 ml of adjuvant in the plantar area of the right hind paw. The adjuvant was prepared by bead-milling, heat-killed, lyophilized Mycobacterium butyricum (Difco #0640) in light mineral oil (Fisher Scientific Co. #0–119 Paraffin Oil—Saybolt Viscosity 125/135) 5 mg/ml. Twenty non-arthritic control rats were injected with mineral oil. The animals received water and Wayne Lab-Blox ad libitum*.

*while on a 10-hour light—14 hour dark cycle.

The rats were held for 14 days to allow the development of polyarthritis. The volume of the uninjected, left-hind paw of each rat was measured by using a Ugo Basile Volume Differential Meter, Model 7101. Adjuvant injected rats showing no evidence of arthritis were discarded and the arthritic rats were distributed into groups of 10 having equal mean paw volumes with equal standard deviation. Non-arthritic (oil-injected) control rats were distributed to 2 groups of 10. Suspensions of test compounds were prepared for dosing by bead-milling (4 mm glass beads in rubber stoppered serum bottles) for 4–5 hours in aqueous 1% polyvinyl alcohol, 5% gum acacia and 0.5% methylparaben.

Test compounds were given orally by gavage once daily for 7 days (days 14–20). The 2 groups of oil injected, non-arthritic control rats and the 2 groups of arthritic control rats received vehicle only for 7 days. Paw volumes (uninjected left hind paw) were measured 20 hours after the last dose (on day 21).

Percent decrease from control mean paw volume was calculated with the following formula:

$$\frac{\text{Arthritic Vehicle Control Mean Paw Volume (ml)} - \text{Arthritic Treatment Mean Paw Volume (ml)}}{\text{Arthritic Vehicle Control Mean Paw Volume (ml)} - \text{Non-Arthritic Vehicle Control Mean Paw Volume (ml)}} \times 100 =$$

% Decrease from Control Mean Paw Volume

Dose-response regression lines of the percent decrease were plotted on semi-log paper and the $ED_{50}$ percent for decrease from control paw volume was estimated by inspection (see Table 3).

Phenylquinone Writhing Test

A standard procedure for detecting and comparing the analgesic activity of compounds in this series for which there is good correlation with human efficacy in the standard phenylquinone writhing test modified from Siegmund, et al., Proc. Soc. Exp. Biol. Med., 95, 729 (1957). A test compound suspended in 1% methylcellulose-1.25% Tween 80 was given orally to fasted (17-21 hours) female white mice, 5-10 animals per double blind test. Aqueous (0.10% phenyl-p-benzoquinone) phenylquinone was injected intraperitoneally at 24 minutes later using 0.20 ml per mouse. Commencing at 30 minutes after the oral administration of the test compound, the mice were observed for 10 minutes for a characteristic stretching or writhing syndrome which is indicative of pain induced by phenylquinone. The effective analgesic dose for 50% of the mice ($ED_{50}$) was calculated by the moving average method of Thompson, W. R., Bact. Rev., 11, 115-145 (1947). (See Table 3).

TABLE 3
Biological Data

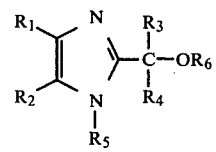

| EXAMPLE | $R_1$ | $R_2$ | $R_3$ | $R_4$ | $R_5$ | $R_6$ | Adjuvant[1] Arthritis $ED_{50}$ mg/kg | Phenylquinone Writhing $ED_{50}$ mg/kg |
|---|---|---|---|---|---|---|---|---|
| 1 | 4-$FC_6H_4$ | 4-$FC_6H_4$ | $CF_3$ | $CF_3$ | H | H | 8.0 | >108 |
| 2 | 4-$CH_3OC_6H_4$ | 4-$CH_3OC_6H_4$ | $CF_3$ | $CF_3$ | H | H | 5.0 | 2.7 |
| 3 | 4-$FC_6H_4$ | 4-$FC_6H_4$ | $CF_3$ | $CH_3$ | H | H | 1.8 | 39 |
| 4 | 4-$CH_3OC_6H_4$ | 4-$CH_3OC_6H_4$ | $CF_3$ | $CF_3$ | $CH_3$ | H | 15 | >135 |
| 5 | 4-$CH_3OC_6H_4$ | 4-$CH_3OC_6H_4$ | $CF_3$ | $CF_3$ | $CH_3$ | —$C(O)CH_3$ | (45%/25) | >108 |
| 6 | 4-$CH_3OC_6H_4$ | 4-$CH_3OC_6H_4$ | $CF_3$ | $CF_3$ | $CH_3$ | —$COOC_2H_5$ | (17%/45)[2] | >108 |
| 7 | 4-$CH_3OC_6H_4$ | 4-$CH_3OC_6H_4$ | $CF_3$ | $CF_3$ | H | $CH_3$ | 4.4 | 32 |
| 10 | 4-$CH_3OC_6H_4$ | 4-$CH_3OC_6H_4$ | $CF_3$ | H | H | H | 45 | 1.9 |
| 11 | 4-$FC_6H_4$ | 4-$FC_6H_4$ | $CF_3CF_2$ | $CH_3$ | H | H | 1.4 | >108 |
| 12 | 4-$CH_3OC_6H_4$ | 4-$CH_3OC_6H_4$ | $CF_3$ | $CF_2Cl$ | H | H | 6.0 | 42 |
| 13 | 4-$CH_3OC_6H_4$ | 4-$CH_3OC_6H_4$ | $CF_2Cl$ | $CF_2Cl$ | H | H | 15 | 135 |
| 14 | 4-$FC_6H_4$ | 2-thienyl | $CF_3$ | $CF_3$ | H | H | 90 | >108 |
| 15 | 4-$CH_3OC_6H_4$ | 4-$CH_3OC_6H_4$ | $CF_3$ | $CF_2H$ | H | H | 3.0 | 1.4 |
| 16 | 4-$FC_6H_4$ | 4-$FC_6H_4$ | $CF_3$ | $CF_2H$ | H | H | 4.8 | >108 |
| 17 | $C_6H_5$ | 3,4-$Cl_2C_6H_3$ | $CF_3$ | $CF_3$ | H | H | (21%/50) | — |
| 18 | 4-$CH_3OC_6H_4$ | 4-$CH_3OC_6H_4$ | $CF_3$ | $CH_3$ | H | H | 5.4 | 2.2 |
| 19 | 4-$CH_3OC_6H_4$ | 4-$CH_3OC_6H_4$ | $CF_3$ | H | $CH_3$ | H | (0%/27)[2] | >108 |
| 20 | $C_6H_5$ | $C_6H_5$ | $CF_3$ | $CF_3$ | H | H | 27 | 57 |
| 21 | 4-$FC_6H_4$ | 4-$CH_3SC_6H_4$ | $CF_3$ | $CF_3$ | H | H | (61%/15) | — |
| 22 | 4-$ClC_6H_4$ | 4-$ClC_6H_4$ | $CF_3$ | $CF_3$ | H | H | (37%/9) | >135 |
| 23 | 4-$FC_6H_4$ | 4-$FC_6H_4$ | $CF_3CF_2$ | H | H | H | 6.8 | 24 |
| 24 | 4-$FC_6H_4$ | 4-$CH_3SC_6H_4$ | $CF_3$ | $CH_3$ | H | H | (51%/9) | 102 |
| 25 | 4-$FC_6H_4$ | 4-$FC_6H_4$ | $CF_3$ | $CF_3$ | H | $C(O)CH_3$ | 13 | >108 |
| 26 | 4-$FC_6H_4$ | 4-$FC_6H_4$ | $CH_3$ | $CH_3$ | $CH_3$ | H | (47%/25) | >108 |
| 27 | 4-$FC_6H_4$ | 4-$FC_6H_4$ | $CF_3$ | H | H | H | 14 | >108 |
| 28 | 4-$FC_6H_4$ | 4-$FC_6H_4$ | $CH_3$ | $CH_3$ | H | H | (48%/50) | >108 |
| 29 | 4-$CH_3OC_6H_4$ | 4-$CH_3OC_6H_4$ | $CF_3CF_2$ | $CH_3$ | H | H | 15 | 3.5 |
| 30 | 4-$CH_3OC_6H_4$ | 4-$CH_3OC_6H_4$ | $CH_3$ | $CH_3$ | H | H | 6.4 | 4.6 |
| 31 | 4-$FC_6H_4$ | 4-$FC_6H_4$ | $CF_3$ | $CH_3CH_2$ | H | H | 1.7 | >108 |
| 32 | 4-$FC_6H_4$ | 4-$FC_6H_4$ | $CF_3$ | $CH_3CH_2CH_2$ | H | H | 8.6 | >108 |
| 33 | 4-$CH_3OC_6H_4$ | 4-$CH_3OC_6H_4$ | $CH_3$ | 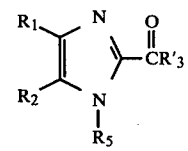 | H | H | (46%/9) | 5.6 |
| 34 | 4-$CH_3OC_6H_4$ | 4-$CH_3OC_6H_4$ | $CH_3$ | $CH_3CH_2$ | H | H | (82%/50) | 5.2 |
| 35 | 4-$CH_3OC_6H_4$ | 4-$CH_3OC_6H_4$ | $CH_3$ | H | H | H | 3.6 | 26 |

[1] Values in parentheses represent the percent reduction in paw volume at the indicated dose.
[2] Although not statistically significantly active at the doses tested, these compounds are expected to be active at higher doses.

TABLE 4
Biological Data

| Example | $R_1$ | $R_2$ | $R'_3$ | $R_5$ | Adjuvant[1] Arthritis $ED_{50}$ mg/kg | Phenylquinone Writhing $ED_{50}$ mg/kg |
|---|---|---|---|---|---|---|
| 8 | 4-$FC_6H_4$ | 4-$FC_6H_4$ | $CF_3$ | H | (49%/25) | >108 |

TABLE 4-continued

Biological Data

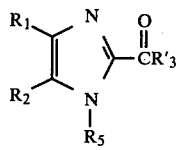

| Example | $R_1$ | $R_2$ | $R'_3$ | $R_5$ | Adjuvant[1] Arthritis $ED_{50}$ mg/kg | Phenyl-quinone Writhing $ED_{50}$ mg/kg |
|---|---|---|---|---|---|---|
| 9 | 4-$CH_3OC_6H_4$ | 4-$CH_3OC_6H_4$ | $CF_3$ | H | 25 | >108 |
| 36 | 4-$CH_3OC_6H_4$ | 4-$CH_3OC_6H_4$ | $CF_3$ | $CH_3$ | (28%/25) | >108 |
| 37 | 4-$FC_6H_4$ | 4-$CH_3SC_6H_4$ | $CF_3$ | H | (24%/25) | >108 |
| 38 | 4-$CH_3OC_6H_4$ | 4-$CH_3OC_6H_4$ | $CF_3CF_2$ | H | (62%/25) | 2.3 |
| 39 | 4-$FC_6H_4$ | 4-$FC_6H_4$ | $CF_3CF_2$ | H | 3.0 | — |
| 40 | 4-$CH_3OC_6H_4$ | 4-$CH_3OC_6H_4$ | $CH_3$ | H | (56%/50) | >135 |
| 41 | 4-$FC_6H_4$ | 4-$FC_6H_4$ | $CH_3$ | H | (0%/25)[2] | — |

[1]Values in parenthesis represent the percent reduction in paw volume at the indicated dose.
[2]Although not active at the dose tested, this compound is expected to be active at higher doses.

What is claimed is:

1. A compound of the formula

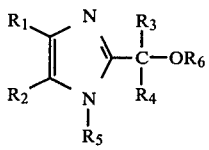

wherein $R_1$ and $R_2$ independently are 3-pyridyl, 2-thienyl or

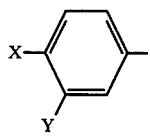

where
X is H, F, Cl, Br, $C_1$–$C_2$ alkyl, $C_1$–$C_2$ alkoxy, di($C_1$–$C_2$ alkyl)amino or $CH_3S(O)_n$;
n=0, 1 or 2;
Y is H, F or Cl with the proviso that when Y is F or Cl, then X must be F or Cl;
$R_3$ and $R_4$ independently are H, $C_1$–$C_3$ alkyl, cyclopropyl, $CF_3$, $CF_2H$, $CF_2Cl$, $CF_3CF_2$ or $CF_3CF_2CF_2$;
with the proviso that no more than one of $R_3$ and $R_4$ can be H;
$R_5$ = H or $C_1$–$C_3$ alkyl;
$R_6$ = H; $C_1$–$C_3$ alkyl;

or —$COOR_7$;
where
$R_7$ is $C_1$–$C_2$ alkyl; with the proviso that
$R_5$ and $R_6$ cannot both be $C_1$–$C_3$ alkyl; a pharmaceutically suitable acid addition salt where $R_1$ or $R_2$ is 3-pyridyl or where X is dialkylamino, or a pharmaceutically suitable metal salt thereof when at least one of $R_5$ and $R_6$ is H.

2. A compound of claim 1 where $R_1$ and $R_2$ independently=

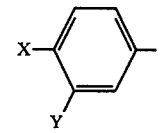

where X is F or $CH_3O$ and Y is H.

3. A compound of claim 1 where $R_3$ and $R_4$ independently are H, $CH_3$, $CH_3CH_2$, $CF_3$, $CF_2H$, $CF_2Cl$ or $CF_2CF_3$.

4. A compound of claim 1 where $R_5$=H.

5. A compound of claim 1 where $R_6$ is H or $CH_3$.

6. A compound of claim 1 where $R_1$ and $R_2$ independently=

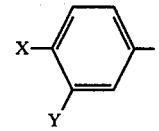

where X is F or $CH_3O$; Y is H; $R_3$ and $R_4$ independently are H, $CH_3$, $CH_3CH_2$, $CF_3$, $CF_2H$, $CF_2Cl$ or $CF_2CF_3$; $R_5$=H; $R_6$ is H or $CH_3$.

7. The compound of claim 1 which is 4,5-bis(4-fluorophenyl)-α,α-di(trifluoromethyl)-1H-imidazole-2-methanol.

8. The compound of claim 1 which is 4,5-bis(4-fluorophenyl)-α-methyl-α-pentafluoroethyl-1H-imidazole-2-methanol.

9. The compound of claim 1 which is 4,5-bis(4-fluorophenyl)-α-ethyl-α-trifluoromethyl-1H-imidazole-2-methanol.

10. A pharmaceutical composition consisting essentially of a suitable pharmaceutical carrier and an effective antiinflammatory amount of a compound of claim 1.

11. A pharmaceutical composition consisting essentially of a suitable pharmaceutical carrier and an effective antiinflammatory amount of a compound of claim 2.

12. A pharmaceutical composition consisting essentially of a suitable pharmaceutical carrier and an effective antiinflammatory amount of a compound of claim 3.

13. A pharmaceutical composition consisting essentially of a suitable pharmaceutical carrier and an effective antiinflammatory amount of a compound of claim 4.

14. A pharmaceutical composition consisting essentially of a suitable pharmaceutical carrier and an effective antiinflammatory amount of a compound of claim 5.

15. A pharmaceutical composition consisting essentially of a suitable pharmaceutical carrier and an effective antiinflammatory amount of a compound of claim 6.

16. A pharmaceutical composition consisting essentially of a suitable pharmaceutical carrier and an effective antiinflammatory amount of the compound of claim 7.

17. A pharmaceutical composition consisting essentially of a suitable pharmaceutical carrier and an effective antiinflammatory amount of the compound of claim 8.

18. A pharmaceutical composition consisting essentially of a suitable pharmaceutical carrier and an effective antiinflammatory amount of the compound of claim 9.

19. A method of treating inflammation in a mammal which comprises administering to the mammal an antiinflammatory amount of a compound of claim 1.

20. A method of treating inflammation in a mammal which comprises administering to the mammal an antiinflammatory amount of a compound of claim 2.

21. A method of treating inflammation in a mammal which comprises administering to the mammal an antiinflammatory amount of a compound of claim 3.

22. A method of treating inflammation in a mammal which comprises administering to the mammal an antiinflammatory amount of a compound of claim 4.

23. A method of treating inflammation in a mammal which comprises administering to the mammal an antiinflammatory amount of a compound of claim 5.

24. A method of treating inflammation in a mammal which comprises administering to the mammal an antiinflammatory amount of a compound of claim 6.

25. A method of treating inflammation in a mammal which comprises administering to the mammal an antiinflammatory amount of the compound of claim 7.

26. A method of treating inflammation in a mammal which comprises administering to the mammal an antiinflammatory amount of the compound of claim 8.

27. A method of treating inflammation in a mammal which comprises administering to the mammal an antiinflammatory amount of the compound of claim 9.

28. A compound of claim 1 where $R_1$ and $R_2$ are both

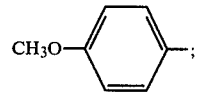

$R_3$ and $R_4$ independently are H, $CH_3$, $CH_3CH_2$, $CF_2H$, $CF_3$ or $CF_2CF_3$; $R_5=H$; and $R_6$ is H or $CH_3$.

29. The compound of claim 28 which is 4,5-bis(4-methoxyphenyl)-α,α-di(trifluoromethyl)-1H-imidazole-2-methanol.

30. The compound of claim 28 which is 4,5-bis(4-methoxyphenyl)-α-difluoromethyl-α-trifluoromethyl-1H-imidazole-2-methanol.

31. A pharmaceutical composition consisting essentially of a suitable pharmaceutical carrier and an effective analgesic amount of a compound of claim 28.

32. A pharmaceutical composition consisting essentially of a suitable pharmaceutical carrier and an effective analgesic amount of the compound of claim 29.

33. A pharmaceutical composition consisting essentially of a suitable pharmaceutical carrier and an effective analgesic amount of the compound of claim 30.

34. A method of alleviating pain in a mammal which comprises administering to the mammal an analgesic amount of a compound of claim 28.

35. A method of alleviating pain in a mammal which comprises administering to the mammal an analgesic amount of the compound of claim 29.

36. A method of alleviating pain in a mammal which comprises administering to the mammal an analgesic amount of the compound of claim 30.

* * * * *